United States Patent [19]

Hadley et al.

[11] Patent Number: 4,599,420
[45] Date of Patent: Jul. 8, 1986

[54] AZABICYCLIC INTERMEDIATES FOR PHARMACEUTICAL COMPOUNDS

[75] Inventors: Michael S. Hadley, Sawbridgeworth; Francis D. King, Newport, both of England

[73] Assignee: Beecham Group Ltd., England

[21] Appl. No.: 469,681

[22] Filed: Feb. 25, 1983

Related U.S. Application Data

[60] Division of Ser. No. 271,990, Jun. 9, 1981, Pat. No. 4,544,660, which is a continuation-in-part of Ser. No. 107,413, Dec. 26, 1979, Pat. No. 4,273,778.

[30] Foreign Application Priority Data

Dec. 30, 1978 [GB] United Kingdom ............... 50380/78
Mar. 15, 1979 [GB] United Kingdom ............... 7909262
Aug. 9, 1979 [GB] United Kingdom ............... 7927831

[51] Int. Cl.$^4$ ........................................... C07D 451/14
[52] U.S. Cl. ........................ 546/124; 546/112; 546/133; 260/239 BF; 548/515
[58] Field of Search ........................................ 546/124

[56] References Cited

PUBLICATIONS

March, Advanced Organic Chemistry: Reactions, Mechanisms and Structure, McGraw-Hill Pub., pp. 899–900, (1968).

P. A. S. Smith, The Chemistry of Open-Chain Organic Nitrogen Compounds, vol. I, Benjamin Pub., p. 65, (1965).

Chem. Abstracts, vol. 52(1), p. 1291-c-g, Jan. 10, 1958.

*Primary Examiner*—Alan L. Rotman
*Attorney, Agent, or Firm*—Jacobs & Jacobs

[57] ABSTRACT

This invention relates to novel substituted benzamides having useful pharmacological properties, to pharmaceutical compositions containing them, to a process for their preparation and to intermediates therefor.

N-(2-Diethylaminoethyl)-2-methoxy-4-amino-5-chlorobenzamide, 1-ethyl-2(2-methoxy-5-sulphamoylbenzamidomethyl)pyrrolidine and N-[4'-(1"-benzyl)-piperidyl]-2-methoxy-4-amino-5-chlorobenzamide are well known compounds having useful pharmacological activity such as the ability to regulate the gastro-intestinal function anti-emetic activity and CNS activity.

It has now been found that certain intermediates for a structurally distinct class of substituted benzamides also has useful pharmacological activity, in particular dopamine antagonist activity.

5 Claims, No Drawings

AZABICYCLIC INTERMEDIATES FOR PHARMACEUTICAL COMPOUNDS

CROSS REFERENCE TO RELATED APPLICATIONS

This application is a division of Ser. No. 06,271,990 filed 06-09-81, now U.S. Pat. No. 4,544,660 issued 10-01-85, which in-turn is a continuation-in-part of Ser. No. 06/107,413 filed 12-26-79, now U.S. Pat. No. 4,273,778 issued 06-16-81.

Accordingly, the present invention provides a compound of the formula (I), and pharmaceutically acceptable salts thereof:

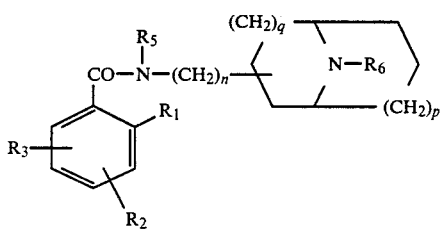

wherein:
$R_1$ is a $C_{1-6}$ alkoxy group;
$R_2$ and $R_3$ are the same or different and are hydrogen, halogen, $CF_3$, $C_{2-7}$ acyl, $C_{2-7}$ acylamino, or amino, aminocarbonyl or aminosulphone optionally substituted by one or two $C_{1-6}$ alkyl groups, $C_{1-6}$ alkylsulphone or nitro;
$R_5$ is hydrogen or $C_{1-6}$ alkyl;
$R_6$ is $C_{1-7}$ alkyl or a group $—(CH_2)_sR_7$ where s is 0 to 2 and $R_7$ is a $C_{3-8}$ cycloalkyl group, or a group $—(CH_2)_tR_8$ where t is 1 or 2 and $R_8$ is $C_{2-5}$ alkenyl or a phenyl group optionally substituted by one or two substituents selected from $C_{1-6}$ alkyl, $C_{1-4}$ alkoxy, trifluoromethyl and halogen; and
n, p and q are independently 0 to 2.

Suitable examples of the group $R_1$ include methoxy, ethoxy and n- and iso-propoxy. Preferably $R_1$ is a methoxy group.

Suitable examples of the groups $R_2$ and $R_3$ include the following groups: hydrogen, chlorine, bromine, $CF_3$, acetyl, propionyl, n- and iso-butyryl, acetylamino, propionylamino, n- and iso-butyrylamino, amino, aminocarbonyl, aminosulphone, amino, aminocarbonyl and aminosulphone substituted by one or two methyl, ethyl, n- or iso-propyl, n-, sec- or tert-butyl groups; and methyl, ethyl or n- and iso-propylsulphones, and nitro.

Particularly suitable $R_2$ and $R_3$ groups include hydrogen, halogen, acyl, amino, and acylated amino as defined.

It is generally preferred that $R_2$ is in the 4-position relative to the carbonyl side chain for greater activity in the resultant compound of the formula (I). For the same reason it is generally preferred that $R_3$ is in the 5-position relative to the carbonyl side chain.

Particularly preferred $R_2$ groups include 4-amino and 4-(acylated amino) as defined. Preferably $R_2$ is 4-amino. Particularly preferred $R_3$ groups include 5-halo, such as 5-chloro.

Often the amide and side chain nitrogen atoms are separated by a minimum of 2 or 3 carbon atoms, preferably 3.

Suitable examples of $R_5$ include hydrogen, methyl, ethyl, n- and iso-propyl, n-, sec- and tert-butyl, preferably hydrogen or methyl, in particular hydrogen.

Suitable examples of $R_6$ when $C_{1-7}$ alkyl include methyl, ethyl, n- and iso-propyl and n-, sec-, iso- and tert-butyl, n-pentyl, n-hexyl and n-heptyl.

Within $C_{1-7}$ radicals, $C_{1-4}$ alkyl are particularly useful (as hereinafter described).

Suitable examples of $R_6$ when $C_{1-4}$ alkyl include methyl, ethyl, n- and iso-propyl and n-, sec-, iso- and tert-butyl, particularly methyl, n-propyl and iso-butyl.

Similarly, within $C_{1-7}$ radicals, $C_{5-7}$ alkyl are also of interest (as hereinafter described).

Suitable examples of $R_6$ when $C_{5-7}$ alkyl include n-pentyl, n-hexyl and n-heptyl.

When $R_6$ is a group $—(CH_2)_sR_7$ as defined, suitable examples of $R_7$ include $C_{5-8}$ cycloalkyl, preferably cyclohexyl, s is preferably 1.

When $R_6$ is a group $—(CH_2)_tR_8$ as defined, t is preferably 1.

In such a group $R_6$, when $R_8$ is $C_{2-5}$ alkenyl, suitable examples thereof include vinyl, prop-1-enyl, prop-2-enyl, 1-methylvinyl, but-1-enyl, but-2-enyl, but-3-enyl, 1-methylenepropyl, 1-methylprop-1-enyl and 1-methylprop-2-enyl, in their E and Z forms where stereoisomerism exists.

A preferred $C_{1-5}$ alkenyl $R_8$ radical is vinyl, so that $R_6$ is preferably allyl.

When $R_8$ is optionally substituted phenyl as defined above, suitable examples of such optional phenyl substituents include methyl, ethyl, n- and iso-propyl, n-, sec- and tert-butyl; methoxy, ethoxy, n- and iso-propoxy; $CF_3$; fluoro, chloro or bromo. Preferably $R_8$ when optionally substituted phenyl is unsubstituted.

Compounds of the formula (I) wherein $R_6$ is $—(CH_2)_sR_7$ and $—(CH_2)_tR_8$ as defined, and wherein $R_6$ contains at least 5 carbon atoms, are of particular interest because of their beneficial pharmacological activity (as hereinafter discussed). In such compounds $R_6$ is preferably benzyl.

n is preferably 0. q is suitably 0 to 1, preferably 1. p is suitably 0 to 1, preferably 0.

It is greatly preferred for higher activity that the bond between the benzamide moiety and the cyclic side chain (i.e. between the $R_5$ substituted nitrogen atom and the $(CH_2)_n$ moiety) in the compounds of formula (I) is equatorial.

The pharmaceutically acceptable salts of the compounds of the formula (I) include acid addition salts with conventional acids such as hydrochloric, hydrobromic, phosphoric, sulphuric, citric, tartaric, lactic and acetic acid and the like.

The pharmaceutically acceptable salts of the compounds of the formula (I) also include quaternary ammonium salts. Examples of such salts include such compounds quaternised by compounds such as $R_9$—Y wherein $R_9$ is $C_{1-6}$ alkyl, phenyl—$C_{1-6}$ alkyl or $C_{5-7}$ cycloalkyl, and Y is an anion of an acid. Suitable examples of $R_9$ include methyl, ethyl and n- and iso-propyl; and benzyl and phenylethyl. Suitable examples of Y include the halides such as chloride, bromide and iodide.

Examples of pharmaceutically acceptable salts also include internal salts such as N-oxides.

The compounds of the formula (I) can also form hydrates.

A group of compounds within those of the formula (I) consists of those wherein:

$R_1$ is a $C_{1-6}$ alkoxy group;

$R_2$ and $R_3$ are the same or different and are hydrogen, halogen, $CF_3$, $C_{2-7}$ acyl, amino, $C_{2-7}$acyl amino, aminocarbonyl or aminosulphone optionally substituted by one or two $C_{1-6}$ alkyl groups; $C_{1-6}$ alkylsulphone or nitro groups;

$R_5$ is hydrogen or $C_{1-6}$ alkyl;

$R_6$ is $C_{1-7}$ alkyl or a group $-(CH_2)_sR_7$ where s is 1 or 2 and $R_7$ is a $C_{3-8}$ cycloalkyl group, or a phenyl group optionally substituted by one or two substitutents selected from $C_{1-6}$ alkyl, $C_{1-4}$ alkoxy, trifluoromethyl and halogen; and n, p and q are independently 0 to 2.

From the aforesaid it will be seen that in a preferred aspect the moiety of formula (II):

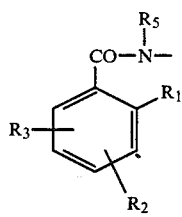
(II)

in a compound of the formula (I) will have the structure (III):

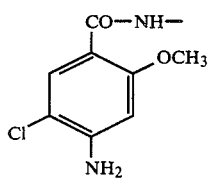
(III)

In a preferred group of compounds within those of formula (I) and pharmaceutically acceptable salts thereof, the moiety of formula (II) will be of the formula (III), and the moiety of formula (IV):

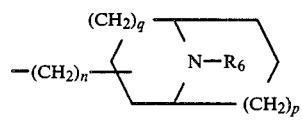
(IV)

will have the formula (V):

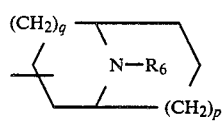
(V)

wherein the variables are as defined in formula (I), so that these preferred compounds of the formula (I) are of the formula (VI):

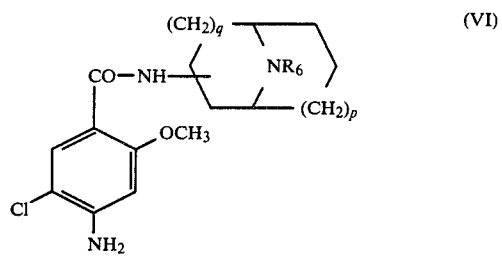
(VI)

wherein the variables are as defined in formula (I).

More suitably p is 0 or 1, it is believed preferably 0.

Preferably q is 1 and the moiety of formula (III) is then attached at a position para to the N-atom.

Suitable and preferred examples of $R_6$ in formula (VI) include those listed under formula (I) for $R_6$. Particularly preferred examples of $R_6$ include $C_{1-7}$ alkyl and cyclohexylmethyl. Particularly preferred examples of $R_6$ also include benzyl optionally substituted in the phenyl ring as defined under formula (I). Unsubstituted benzyl is especially preferred.

A particularly preferred sub-group of compounds within those of formula (VI) are those of the formula (VII):

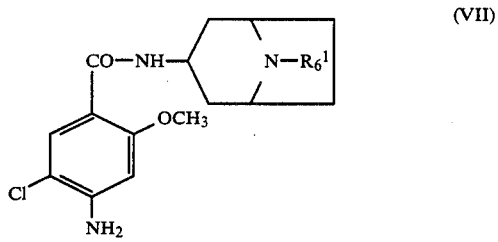
(VII)

wherein $R^1_6$ is $C_{1-4}$ alkyl.

Suitable examples of $R^1_6$ are as so described for $R_6$ $C_{1-4}$ alkyl under formula (I).

It is preferred that the moiety of the formula (III) is in the β-orientation to the nortropane ring.

Another particularly preferred sub-group of compounds within those of formula (VI) are those of the formula (VIII):

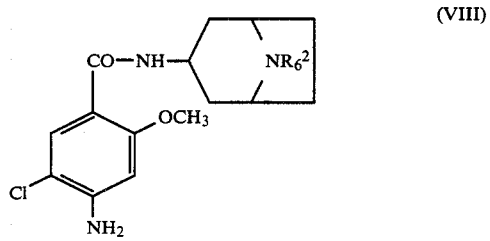
(VIII)

wherein $R^2_6$ is $C_{5-7}$ alkyl; a group $-(CH_2)_tR^1_8$ wherein t is 1 or 2 and $R^1_8$ is optionally substituted phenyl as defined in formula (I); or cyclohexylmethyl.

Suitable and preferred $R^2_6$ are as so described for the corresponding $R_6$ groups under formula (I).

R²₆ benzyl is especially preferred.

It is preferred that the moiety of the formula (III) is in the β-orientation to the nortropane ring.

A sub-group of compounds within those of the formula (VI) of interest are those of the formula (IX):

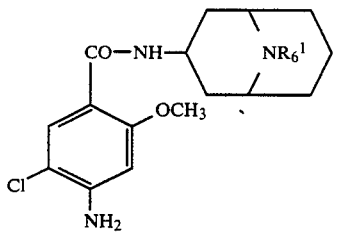

wherein R₆¹ is as defined in formula (VII).

Suitable examples of R₆¹ are as so described under formula (VII).

Another sub-group of compounds within those of the formula (VI) of interest are those of the formula (X):

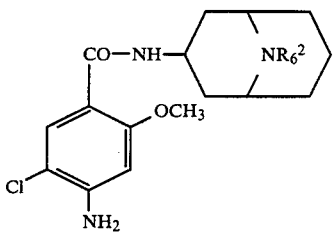

wherein R²₆ is as defined in formula (VIII).

Suitable and preferred examples of R²₆ are as so described under formula (VIII). Benzyl is especially preferred.

In a second group of compounds of interest the moiety of formula (II) will have the structure (III) as hereinbefore depicted and defined, but the moiety of formula (IV) will have the structure (XI):

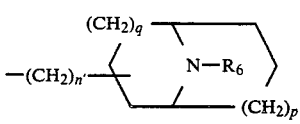

wherein n' is 1 or 2 and the remaining variables are as defined in formula (I).

More suitably p and q independently are 0 or 1; preferably p is 0 and q is 1.

Suitably and preferred examples of R₆ include those listed hereinbefore for R₆. Particularly preferred examples of R₆ include benzyl optionally substituted in the phenyl ring as defined under formula (I). Unsubstituted benzyl is expecially preferred.

Particularly suitable examples of the compounds of the present invention include those specifically prepared in the Examples which form a later section in this specification. These are:

4-acetamido-5-chloro-2-methoxy-N-(3α-[8'-benzyl-8'-azabicyclo[3.2.1]octyl])benzamide,
4-acetamido-5-chloro-2-methoxy-N-(3'β-[8'-benzyl-8'-azabicyclo[3.2.1]octyl])benzamide,
4-amino-5-chloro-2-methoxy-N-(3'α-[8'-benzyl-8'-azabicyclo[3.2.1]octyl])benzamide,
4-amino-5-chloro-2-methoxy-N-(3'β-[8'-benzyl-8'-azabicyclo[3.2.1]octyl])benzamide,
4-amino-5-chloro-2-methoxy-N-methyl-(3'α-[8'-benzyl-8'-azabicyclo[3.2.1]octyl])benzamide,
4-amino-5-chloro-2-methoxy-N-methyl-(3'-β-[8'-benzyl-8'-azabicyclo[3.2.1]octyl])benzamide,
5-sulphamoyl-2-methoxy-N-(3'β-[8'-benzyl-8'-azabicyclo[3.2.1]octyl])benzamide,
2-methoxy-N-(3'β-[8'-benzyl-8'-azabicyclo[3.2.1]octyl])benzamide
4-amino-5-chloro-2-methoxy-N-(3'β-[8'-benzyl-8'-azabicyclo[3.2.1]octyl])benzyl methobromide
4-amino-5-chloro-2-methoxy-N-(3α'-[9'-benzyl-9'-azabicyclo[3.3.1]nonyl])benzamide,
4-amino-5-chloro-2-methoxy-N-(3β'-[9'-benzyl-9'-azabicyclo[3.3.1]nonyl])benzamide,
4-amino-5-chloro-2-methoxy-N-(3'β-[8'-[4''-methylbenzyl]-8'-azabicyclo-[3.2.1]-octyl])-benzamide,
4-amino-5-chloro-2-methoxy-N-(3'β-[8'[4''-methoxybenzyl]-8'-azabicyclo-[3.2.1]-octyl])-benzamide,
4-amino-5-chloro-2-methoxy-N-(3'β-[8'-[4''-ethoxybenzyl]-8'-azabicyclo-[3.2.1]octyl])-benzamide,
4-amino-5-chloro-2-methoxy-N-(3'β-[8'[4''-chlorobenzyl]-8'-azabicyclo-[3.2.1]octyl])-benzamide,
4-amino-5-chloro-2-methoxy-N-(3'β-[8'-[3'',4''-dichlorobenzyl]-8'-azabicyclo-[3.2.1]octyl])-benzamide.
4-amino-5-chloro-2-methoxy-N-(3'β-[8'-β-phenethyl]-8'-azabicyclo-[3.2.1]-octyl])-benzamide,
4-acetamido-5-chloro-2-methoxy-N-(3'β-[8'-β-phenethyl]-8'-azabicyclo-[3.2.1]-octyl])-benzamide,
4-amino-5-chloro-2-methoxy-N-(3'β-[8'-methyl-8'-azabicyclo[3.2.1]-octyl])-benzamide,
4-amino-5-chloro-2-methoxy-N-(3'α-[8'-methyl-8'-azabicyclo[3.2.1]-octyl])-benzamide
4-acetamido-5-chloro-2-methoxy-N-(3'α-[8'methyl-8'-azabicyclo[3.2.1]octyl])benzamide,
4-amino-5-chloro-2-methoxy-N-(3'α-[9'-methyl-9'-azabicyclo[3.3.1]nonyl])benzamide,
4-amino-5-chloro-2-methoxy-N-(3'β-[9'-methyl-9'-azabicyclo[3.3.1]-nonyl])-benzamide,
4-amino-5-chloro-2-methoxy-N-(3'β-[8'-ethyl-8'-azabicyclo[3.2.1]octyl])benzamide,
4-acetamido-5-chloro-2-methoxy-N-(3'β-[8'-ethyl-8'-azabicyclo[3.2.1]octyl])benzamide,
4-amino-5-chloro-2-methoxy-N-(3'β-[8'-n-propyl-8'-azabicyclo[3.2.1]-octyl])benzamide,
4-acetamido-5-chloro-2-methoxy-N-(3'β-[8'-n-propyl-8'-azabicyclo[3.2.1]-octyl)benzamide,
4-amino-5-chloro-2-methoxy-N-(3'β-[8'-iso-propyl-8'-azabicyclo[3.2.1]-octyl])benzamide
4-amino-5-chloro-2-methoxy-N-(3'β-[8'-n-butyl-8'-azabicyclo[3.2.1]-octyl])benzamide,
4-amino-5-chloro-2-methoxy-N-(3'α-[8'-n-butyl-8'-azabicyclo[3.2.1]-octyl])benzamide,
4-amino-5-chloro-2-methoxy-N-(3'β-[8'-secbutyl-8'-azabicyclo-[3.2.1]-octyl])-benzamide
4-amino-5-chloro-2-methoxy-N-(3'β-[8'-isobutyl-8'-azabicyclo-[3.2.1]-octyl])-benzamide,
4-amino-5-chloro-2-methoxy-N-(3'β-[8'-cyclohexylmethyl-8'-azabicyclo-[3.2.1]-octyl])-benzamide
4-amino-5-chloro-2-methoxy-N-(3'β-[8'-cyclohexyl-8'-azabicyclo[3.2.1]octyl])benzamide,
4-acetamido-5-chloro-2-methoxy-N-(3'β-[8'-cyclohexyl-8'-azabicyclo[3.2.1]octyl]benzamide, 4-amino-5-chloro-2-methoxy-N-(3′β-[8′-allyl-S-azabicyclo[3.2.1]octyl])benzamide, 5-chloro-2-methoxy-4-methylamino-N-(3β-[8′-benzyl-8-azabicyclo[3.2.1]octyl])benzamide, 4-amino-5-chloro-2-methoxy-N-(2′-(+)-α-[8′-benzyl-8′-azabicyclo[3.2.1]octyl]methyl)benzamide, 4-amino-5-chloro-2-methoxy-N-(2′-(−)-α-[8′-benzyl-8′-azabicyclo[3.2.1]octyl]methyl)benzamide, 4-amino-5-chloro-2-methoxy-N-(2′-(+)-β-[8′-benzyl-8′-azabicyclo[3.2.1]octyl]methyl)benzamide, 4-amino-5-chloro-2-methoxy-N-(2′-(−)-β-[8′-benzyl-8′-azabicyclo[3.2.1]octyl]methyl)benzamide, 4-amino-5-chloro-2-methoxy-N-(2′-(+)-α-[8′-methyl-8′-azabicyclo[3.2.1]octyl]methyl)benzamide, 4-amino-5-chloro-2-methoxy-N-(2′-(−)-α-[8′-methyl-8′-azabicyclo[3.2.1]octyl]methyl)benzamide, 4-amino-5-chloro-2-methoxy-N-(2′-(+)-β-[8′-methyl-8′-azabicyclo[3.2.1]octyl]methyl)benzamide, 4-amino-5-chloro-2-methoxy-N-(2′-(−)-β-[8′-methyl-8′-azabicyclo[3.2.1]octyl]methyl)benzamide, 4-amino-5-chloro-2-methoxy-N-(2′-(+)-α-[7′-benzyl-7′-azabicyclo[2.2.1]heptyl])benzamide, 4-amino-5-chloro-2-methoxy-N-(2′-(−)-α-[7′-benzyl-7′-azabicyclo[2.2.1]heptyl])benzamide, 4-amino-5-chloro-2-methoxy-N-[2′-(+)-β-[7′-benzyl-7′-azabicyclo[2.2.1]heptyl])benzamide, 4-amino-5-chloro-2-methoxy-N-(2′-(−)-β-[7′-benzyl-7′-azabicyclo[2.2.1]heptyl])benzamide, 4-amino-4-chloro-2-methoxy-N-(4′-(+)-α-[9′-benzyl-9′-azabicyclo[4.2.1]nonyl])benzamide, 4-amino-5-chloro-2-methoxy-N-(4′-(−)-α-[9′-benzyl-9′-azabicyclo[4.2.1]nonyl])benzamide, 4-amino-5-chloro-2-methoxy-N-(4′-(+)-β-[9′-benzyl-9′-azabicyclo[4.2.1]nonyl])benzamide, and 4-amino-5-chloro-2-methoxy-N-(4′-(−)-β-[9′-benzyl-9′-azabicyclo[4.2.1]nonyl])benzamide.

It will of course be realised that the compounds of the formula (I) have chiral or prochiral centres, and thus are capable of existing in a number of stereoisomeric forms. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

The invention also provides a process for the preparation of a compound of the formula (I), which process comprises reacting an acid of the formula (XII):

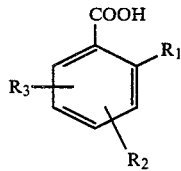

(XII)

or a reactive derivative thereof, with a compound of formula (XIII):

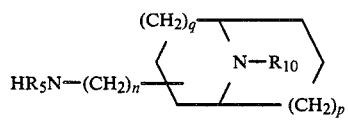

(XIII)

wherein $R_{10}$ is hydrogen or $R_6$ as defined in formula (I), the remaining variable groups being as defined in formula (I); and thereafter if desired or necessary converting a group $R_2$ or $R_3$ in the thus formed compound to another group $R_2$ or $R_3$ respectively; converting $R_{10}$ when hydrogen to $R_6$; and optionally forming a pharmaceutically acceptable salt of the resultant compound of the formula (I).

'Reactive derivative' when used herein means a derivative of the compound (XII) which can be reacted with the compound (XIII) to form an amido linkage between the acid group of the compound (XII) and the amino group of the compound of the formula (XIII).

Often this reactive derivative will be the acid halide, such as the acid chloride, of the acid (XII). In such cases, the reaction will normally be carried out in an inert solvent, preferably in the presence of an acid acceptor. The inert solvent can be any solvent inert to both reactants, such as benzene, toluene, diethyl ether or the like. The acid acceptor is suitably an organic base such as a tertiary amine e.g. triethylamine, trimethylamine, pyridine or picoline, or an inorganic acid acceptor, such as calcium carbonate, sodium carbonate, potassium carbonate or the like. It should also be noted that it is possible to use certain acid acceptors as the inert solvent, for example organic bases.

Another useful reactive derivative of the acid (XII) that may be used is an ester, such as a methyl, ethyl, propyl or butyl ester, in which case the reaction is normally carried out by heating the reactants together in an inert solvent such as ethylene glycol.

The reaction may also be carried out by forming an anhydride of the acid (XII) in the usual manner, and reacting that with the compound (XIII); normally a conventional mixed anhydride will be used; or by reacting the acid (XII) and the compound (XIII) in the presence of a dehydrating catalyst such as a carbodiimide, for example dicyclohexylcarbodiimide.

The intermediates of the formulae (XII) and (XIII) are either known compounds or can be prepared by analogous processes to known compounds.

It will be realised that in the compound of the formula (I) the —CO—NR$_5$—(CH$_2$)$_n$— linkage may have an α or β orientation with respect to the ring of the bicyclic moiety to which it is attached. A mixture of α and β isomers of the compound of the formula (I) may be synthesised non-stereospecifically and the desired isomer separated conventionally therefrom, e.g. by chromatography; or alternatively the α or β isomer may if desired be synthesised from the corresponding α or β form of the compound of the formula (XIII).

Synthesis from the corresponding α or β isomer of the compound of the formula (XIII) is in general preferred.

The α or β form of the compound of the formula (XIII) may if desired be prepared by known stereospecific processes, such as those leading to the α or β isomers of the compound of the formula (XIII) depicted in the Scheme and described in Descriptions 3C, 4A and 4C and Descriptions 2 and 3A and B respectively.

The precursor of the compound of the formula (XIII) may be stereospecifically synthesised, such as the azide (D3) of Description 2, and then converted to the corresponding desired isomer of the compound of the formula (XIII) under non-stereospecific conditions with retention of configuration. Alternatively, the precursor may itself have no asymmetric centre at the relevant position, such as the oximes and imines of Descriptions 3 and 4, but be converted under stereospecific conditions to the desired isomer of the compound of the formula (XIII).

Alternatively, a mixture of the α and β isomers of the compound of the formula (XIII) may be synthesised non-stereospecifically and the desired isomer separated conventionally therefrom e.g. by chromatography. However, in this case it is generally more convenient to react the mixture to give a mixture of α and β isomers of the compound of the formula (I) and to separate these if desired as hereinbefore described.

The following Scheme 1 illustrates stereospecific and non-stereospecific synthetic routes to intermediates of the formula (XIII) wherein n is 0.

Scheme 1

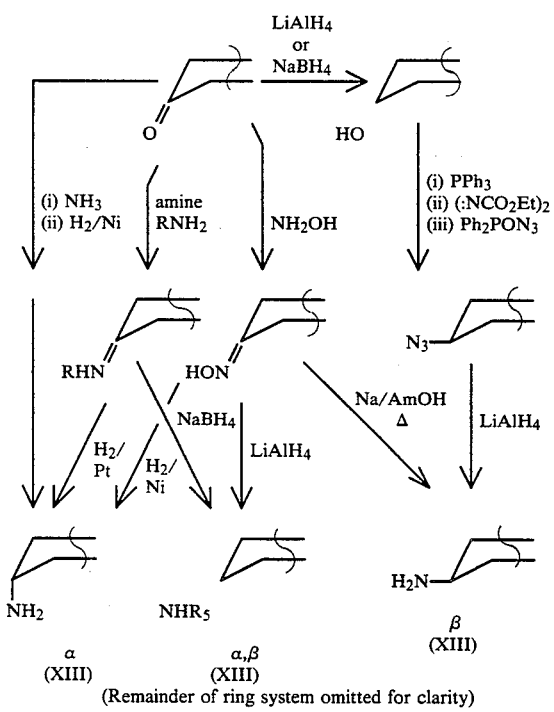

(Remainder of ring system omitted for clarity)

The following Scheme 2 illustrates preparative routes to intermediates of the formula (XIII) wherein n is 1 or 2.

Scheme 2

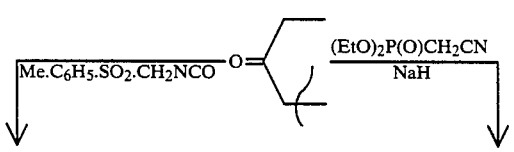

-continued
Scheme 2

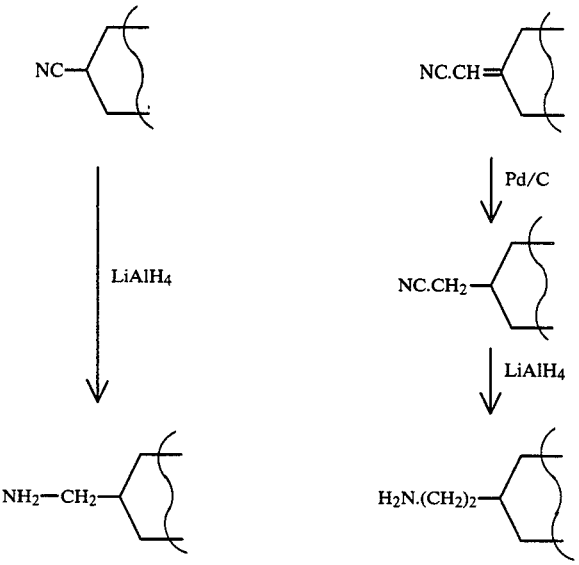

(Remainder of ring system omitted for clarity)

The acid addition salts of compounds of the formula (I) may be prepared in entirely conventional manner by reacting a compound of the formula (I) in base form with the chosen acid.

The quaternary ammonium salts of the compounds of the formula (I) may be prepared in conventional manner for such salts, such as by reaction of the chosen compound of the formula (I) with a compound $R_9Y$ as defined. This reaction is suitably carried out in an appropriate solvent such as acetone, methanol, ethanol, dimethylformamide and the like, at ambient or raised temperature and pressure. The nitrogen atom of the moiety of formula (IV) may also form an N-oxide to give an internal N-oxide salt of the compound of the formula (I). The N-oxides may be prepared in conventional manner such as by reaction of the chosen compound of the formula (I) with an organic per-acid, such as m-chloroperbenzoic acid. This reaction is suitably carried out at below-ambient temperature in an organic solvent, preferably a chlorinated hydrocarbon solvent.

The interconversion of suitable groups $R_2$ and $R_3$ after formation of a compound of the formula (I) or corresponding intermediate therefor may be carried out by conventional methods. By way of example nitro groups may be reduced to amino groups in the normal manner, and acylamino groups may be converted to amino groups also by conventional methods. Also a compound of the formula (I) wherein $R_2$ or $R_3$ is halogen can be prepared by a conventional halogenation of the corresponding compound of the formula (I) wherein the said $R_2$ or $R_3$ is hydrogen. Accordingly it will be realised that compounds of the formula (I) containing an $R_2$ or $R_3$ group which is convertible to another $R_2$ or $R_3$ group are useful intermediates, and as such form an important aspect of the invention.

Conversion of $R_{10}$ when hydrogen to a group $R_6$ as hereinbefore defined may be carried out conventionally, for example by reacting the product of the reaction of the compounds of the formulae (XII) and (XIII) with a compound $QR_6$ wherein $R_6$ is as defined in formula (I) and Q is a group or atom readily displaced by a nucleophile.

Suitable values for Q include Cl, Br, I, $OSO_2CH_3$ or $OSO_2C_6H_4pCH_3$.

Favoured values for Q includes Cl, Br and I.

Particularly suitably the compound $QR_4$ is a benzyl halide such as benzyl bromide or benzyl chloride.

The reaction may be carried out under conventional alkylation conditions for example in an inert solvent such as dimethylformamide in the presence of an acid acceptor such as potassium carbonate. Generally the reaction is carried out at a non-extreme temperature such as at ambient or at a slightly elevated temperature.

It will be appreciated that, when $R_2$ or $R_3$ are converted to other $R_2$ or $R_3$ and $R_5$ being hydrogen is converted to $R_4$, then these conversions may take place in any desired or necessary order.

As hereinbefore stated, the compounds of the formula (I) are dopamine antagonists.

Depending on their balance between peripheral and central action, the compounds of the formula (I) may be used in the treatment of disorders related to impaired gastro-intestinal motility, such as retarded gastric emptying, dyspepsia, flatulence, oesophagal reflux, peptic ulcer and emesis, and/or in the treatment of disorders of the central nervous system, such as psychosis.

All the compounds of the formula (I) may be used in the treatment of emesis.

Examples of compounds of the formula (I) which are of particular interest for their motility enhancing activity are those wherein $R_6$ contains 1 to 4 carbon atoms, such as $C_{1-4}$ alkyl, especially those of formulae (VII) and (IX).

Examples of compounds of the formula (I) which are of particular interest for their CNS activity, and for their anti-emetic activity, are those wherein $R_6$ contains 5 or more carbon atoms, particularly benzyl, such as those of formulae (VIII) and (X).

The invention therefore also provides a pharmaceutical composition comprising a compound of the formula (I), or a hydrate or a pharmaceutically acceptable salt thereof, together with a pharmaceutically acceptable carrier. Such compositions may be adapted for oral or parenteral administration, and as such may be in the form of tablets, capsules, oral liquid preparations, powders, granules, lozenges, reconstitutable powders, injectable and infusable solutions or suspensions and the like; the compositions may also be in the form of suppositories and the like. Normally, orally administrable compositions are preferred.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspension, solutions, emulsions, syrups, or elixirs, or may be presented in a dry product for reconstitution with water or other suitable vehicle before use. Such liquid preparations may contain conventional additives such as suspending agents, emulsifying agents, nonaqueous vehciles (which may include edible oils), preservatives, and if desired conventional flavouring or colouring agents, and the like.

For parenteral administration, fluid unit dosage forms are prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the compound As is common practice, the compositions will usually be accompanied by written or printed directions for use in the medical treatment concerned.

It will of course be realised that the precise dosage used in the treatment of any of the hereinbefore described disorders will depend on the actual compound of the formula (I) used, and also on other factors such as the seriousness of the disorder being treated.

The invention further provides a method of treatment of maladies in humans comprising the administration of an effective amount of a compound of the formula (I) or a pharmaceutically acceptable salt thereof. The "effective amount" will depend in the usual way on a number of factors such as the nature and severity of the malady to be treated, the weight of the sufferer, and the actual compound used.

However by way of illustration, unit doses will suitably contain 0.1 to 20 mgs of the compound of formula (I), for example 0.5 to 10 mgs.

Again by way of illustration, such unit doses will suitably be administered more than once a day, for example 2, 3, 4, 5 or 6 times a day, in such a way that the total daily dose is suitably in the range 0.01 to 10 mg/kg per day.

Compounds of the formula (I) have the ability to potentiate the effect of conventional analgesics in migraine treatment when administered concurrently with the analgesic.

Thus the invention provides a pharmaceutical composition comprising a compound of the formula (I) and an analgesic.

The compound of the formula (I) and the analgesic, such as aspirin or paracetamol, will be present in the composition in amounts generally similar to their usual effective dose.

The composition can be a combination product, for example a tablet or capsule containing both a compound of the formula (I) and an analgesic for oral administration, or a twin pack comprising the two active ingredients made up for separate administration.

The invention accordingly provides a method of treatment of migraine comprising the administration to the sufferer of a compound of the formula (I) and an analgesic.

The following Examples illustrate the preparation of the compounds of formula (I) and the following Descriptions illustrate the preparation of intermediates thereto.

Nomenclature note: Tropane is 8-methyl-8-azabicyclo[3.2.1]octane and derivatives thereof are named accordingly in the following Descriptions

DESCRIPTION 1

3α,β-amino-8-benzyl-8-azabicyclo-[3,2,1]octane (D1); intermediate for Compounds 1 to 3; mixture of 3α-amino-8-benzyl-8-azabicyclo[3.2.1]octane (D26) and 3β-amino-8-benzyl-8-azabicyclo[3.2.1]octane (D4)

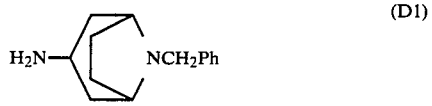

(D1)

8-benzylnortropan-3-one oxime (6 g) was Soxhlet extracted for 15 hours into a stirred suspension of lithium aluminium hydride (2.4 g) in dry THF (150 ml). The mixture was hydrolysed.

Fractional distillation under reduced pressure afforded 3-amino-8-benzylnortropane (D1) (4.2 g, 75%) as a mixture of 3α and 3β isomers. b.pt. 107°–10° C./0.2 mm Hg.

DESCRIPTION 2A

3β-amino-8-benzyl-8-azabicyclo[3.2.1]octane (D4); intermediate for Compounds 4 and 5

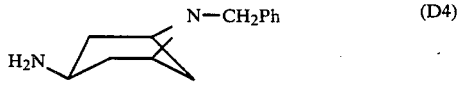

(D4)

(a) 8-benzyl-3-nortropanol (D2)

8-benzyl-3-nortropanone (3.9 g) was reduced with lithium aluminium hydride (1.0 g) in diethyl ether to 8-benzyl-3-nortropanol (D2) by the method of R. Mirza et al., Nature, 1952, 170, 630. This is claimed by Mirza to give stereospecifically the β-isomer but later workers[1] have shown that a mixture of α and β isomers is produced.
[1]A. H. Beckett, N. J. Harper, A. D. J. Babn and T. H. E. Watts, Tetrahedron 1959, 6, 319.

(b) 3β-azido-8-benzylnortropane (D3)

Crude 8-benzyl-3-nortropanol (D2) (3.9 g.) was reacted with successively, triphenylphosphine (4.7 g) and diethyl azodicarboxylate (3.2 g), and diphenylphosphorylazide (5 g) in THF by the method of A. K. Bose et al., Tetrahedron Letters, 1977, 23, 1977, to yield 3β-azido-8-benzylnortropane (D3) as an oil (2 g, 25%). i.r. 2100 cm$^{-1}$ (γN$_3$).

(c) 3β-amino-8-benzylnortropane (D4)

To a stirred suspension of lithium aluminium hydride (0.5 g) in diethyl ether (50 ml) was added a solution of 3β-azido-8-benzylnortropane (D3) (2 g) in diethyl ether (10 ml.), and the reaction was stirred at ambient temperature for 3 hours. Hydrolysis, extraction with ethyl acetate and removal of the solvent afforded crude 3β-amino-8-benzylnortropane (1.1 g, 60%) used in the procedure of Example 2 without further purification. N.B. The assignment of β-configuration to the azide (D3) and amine (D4) is based on the fact that Compound 5 attained via amine (D4) was identical with the β-isomer obtained via the stereospecific route outlined in Description 3β and Example 5.

DESCRIPTION 2B

3β-amino-8-(4'-chlorobenzyl)-8-azabicyclo[3.2.1]octane (D5); intermediate for Compound 16

N-(4-chlorobenzyl)-nortropanone (2.02 g., 8.1 mmole) in methanol (100 ml) was treated with sodium borohydride (0.75 g.). This was stirred at ambient temperature for 12 hours, then poured into saline solution. It was made strongly basic with dilute aqueous sodium hydroxide, and the resulting mixture was extracted with ethyl acetate (3×150 ml). The combined organic extracts were dried (sodium sulphate), filtered and evaporated to yield a mixture of α- and β-N-(4-chlorobenzyl)-nortropanols (2.02 g., 99%).

The mixture of isomeric tropanols from above was converted to 3β-azido-8-(4-chlorobenzyl)-nortropane by the method described in Description 2A. Thus N-(4-chlorobenzyl)-nortropanol (3.3 g., 13.1 mmoles) was successively treated with triphenylphosphine (3.77 g.), diethylazodicarboxylate (2.49 g) and diphenylphosphoryl azide (4.1 g.) in THF to yield, after work up and chromatography to separate the isomeric azide 3β-azido-8-(4-chlorobenzyl)-nortropane (1.1 g., 30.5%) as an oil.

This was reduced with lithium aluminium hydride in ether under reflux for 12 hours. Hydrolysis, extraction with ethyl acetate and removal of solvent afforded crude 3β-amino-8-(4-chlorobenzyl)-nortropane (0.82 g., 82%).

3β-amino-8-(3',4'-dichlorobenzyl)-8-azabicyclo[3.2.1]octane (D6); intermediate for Compound 17 was prepared analogously (32%)

DESCRIPTION 3A

3β-amino-8-methyl-8-azabicyclo[3.2.1]octane (D8), intermediate for Compound 19

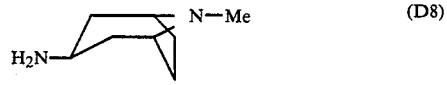

(D8)

(a) Tropinone oxine (D7)

Tropinone (3.68 g; 0.0265 mole) was dissolved in ethanol (50 ml) containing pyridine (4–5 ml) and treated with hydroxylamine hydrochloride (1.90 g). The mixture was heated under reflux for 30 minutes, cooled, treated with solid potassium carbonate (ca. 10 g) and water (ca. 5 ml). The ethanol was removed in vacuo and the mixture extracted with chloroform (3×150 ml). The combined extracts were dried ($K_2CO_3$), filtered and evaporated in vacuo. The resulting solid was recrystallised from ethyl acetate/petrol ether 40-60 to yield tropinoneoxime (3.1 g; 76%) as colourless crystals m.pt 114°-115° C.

(b) 3β-amino-8-methyl-8-azabicyclo[3.2.1]octane (D8)

Tropinone oxime (3.08 g; 0.02 mole) was dissolved in anhydrous amyl alcohol (100 ml) and heated to almost boiling. Sodium (ca. 3.0 g) was added portionwise over 1 hour then the mixture left to cool overnight. The mixture was treated with 5N hydrochloric acid (ca. 80 ml), and extracted with ethyl acetate (3×150 ml). The acidic aqueous layer was separated, basified with sodium hydroxide and re-extracted with ethyl acetate (4×150 ml) and the combined extracts were dried ($K_2CO_3$) filtered and evaporated in vacuo to yield (D8) (2.25 g; 80%) as a colourless oil, used without further purification.

DESCRIPTION 3B

3-β-amino-8-benzyl-8-azabicyclo[3.2.1]octane (D4); intermediate for Compound 5

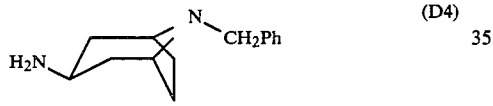

Similarly, sodium (2 g) was added portionwise over 2 hours to a stirred solution of 8-benzylnortropan-3-one oxime (0.9 g) in amyl alcohol (20 ml) at reflux. The solution was cooled diluted, with diethyl ether and acidified with excess dilute hydrochloric acid. The acid extract was washed with diethyl ether and then basified with excess potassium carbonate. Extraction with ethyl acetate followed by evaporation of solvent afforded crude 3β-amino-8-benzylnortropane (d4) (0.85 g) used in the procedure of Example 5 without purification.

The following intermediates were analogously prepared from the corresponding oximes:

3α,β-amino-9-benzyl-9-azabicyclo[3.3.1]nonane (D9) mixture of
3α-amino-9-benzyl-9-azabicyclo[3.3.1]nonane (D10); and 3β-amino-9-benzyl-9-azabicyclo[3.3.1]nonane (D11); intermediates for Compounds 11 and 12 respectivley

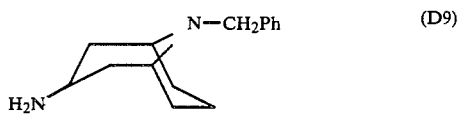

and as oils. The following intermediates of the general formula

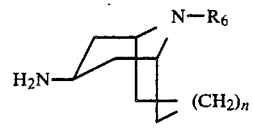

where prepared analogously

| Intermediate No. | $R_6$ | n | For Compound | Yield % |
|---|---|---|---|---|
| D12 | $CH_2$—⟨⟩—Me | 0 | 13 | 97.6 |
| D13 | $CH_2$—⟨⟩—OMe | 0 | 14 | 71 |
| D14 | $CH_2$—⟨⟩—OEt | 0 | 15 | 94 |
| D15 | $CH_2CH_2Ph$ | 0 | 18 | 83 |
| D16 | Me | 1 | 22 | 60 |
| D17 | Et | 0 | 23 | 93 |
| D18 | $Pr^n$ | 0 | 24 | 97 |
| D19 | $Pr^i$ | 0 | 25 | 71 |
| D20 | $Bu^n$ | 0 | 26 | 60 |
| D21 | $CH_2.Pr^i$ | 0 | 28 | 74 |
| D22 | CH(Me)Et | 0 | 29 | 50 |
| D23 | $CH_2$—⟨cyclohexyl⟩ | 0 | 30 | 78 |
| D24 | ⟨cyclohexyl⟩ | 0 | 31 | 66 |
| D30 | $CH_2CH=CH_2$ | 0 | 32 | |

DESCRIPTION 3C 3-amino-9-methyl-9-azabicyclo[3.3.1]nonane (D15); intermediate for Compound 21

N-methyl-9-azabicyclo-[3.3.1]-nonan-3-one oxime (3.25 g., 0.02 mole) was dissolved in ethanol and hydrogenated over Raney nickel in the presence of ammonium acetate at 300 p.s.i. at 50° C. for 24 hours. The mixture was filtered, evaporated in vacuo, dissolved in dilute hydrochloric acid, basified and extracted into ethyl acetate. The combined organic layers were dried ($K_2CO_3$), filtered and evaporated in vacuo to yield 3-amino-9-methyl-9-azabicyclo-[3.3.1]-nonane (2.67 g., 90%), used without further purification.

The product is a single diastereomer believed to be the α-isomer.

DESCRIPTION 3D

3α-amino-9-benzyl-9-azabicyclo[3.3.1]nonane (D10); intermediate for Compound 11

9-Benzyl-9-azabicyclo-(3.3.1)-nonan-3-one oxime (4.0 g; 0.0164 mole), m.p. 134°, was dissolved in ethanol (100 ml) and hydrogenated at 50°-60° at 250 psi in the presence of Raney nickel. The mixture was filtered after 24 hours through kieselguhr and evaporated in vacuo. The resulting oil was dissolved in dilute hydrochloric acid (50 ml) extracted with ethyl acetate (3×150 ml), the aqueous layer was basified and re-extracted with ethyl acetate (3×150 ml). The combined organic extracts were dried (K₂CO₃), filtered and evaporated in vacuo to yield 3-amino-9-benzyl-9-azabicyclo-[3,3,1]-nonane (2.3 g; 61%), used without further purification.

DESCRIPTION 4A

3α-amino-8-benzyl-8-azabicyclo[3.2.1]octane, (D6); intermediate for compound 6

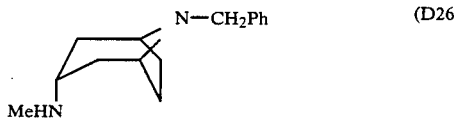

8-benzyl-8-azabicyclo-[3.2.1]-octan-3-one (4.40 g, 0.02 mole) was treated with excess methylamine in ethanol (50 ml), heated to 60°-70°, then hydrogenated in the presence of pre-reduced platinum (400 mg) to give 8-benzyl-3α-methylamino-8-azabicyclo-[3.2.1]-octane (3.33 g, 72%), m.p. 77°-79°.

DESCRIPTION 4B

3α,β-methylamino-8-benzyl-8-azabicyclo[3.2.1]octane (D27); mixture of
3α-methylamino-8-benzyl-8-azabicyclo[3.2.1]octane (D26) and
3β-methylamino-8-benzyl-8-azabicyclo[3.2.1]octane (D28); intermediates for Compounds 6 and 7 respectively

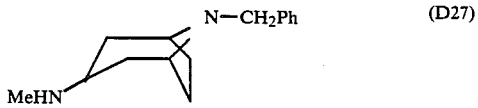

N-benzyl-nortropinone (4.30 g, 0.02 mole) was treated with excess methylamine in anhydrous toluene. Titanium tetrachloride (50 ml of 10% solution in xylene) was added and the mixture stirred for 2 days. The resulting mixture was filtered through kieselguhr and evaporated in vacuo to give N-benzyl-3-methyliminonortropane (5.0 g).

A solution of N-benzyl-3-methylimino-notropane (5.0 g) in methanol (100 ml) was treated portionwise with sodium borohydride (ca 5.0 g) and the mixture left to stir at room temperature for 3 hours. Water (50 ml) was added and the mixture extracted with ether (3×100 ml). The combined organic extracts were dried (K₂CO₃), filtered and evaporated in vacuo to give 3-methylamino-8-benzyl-8-azabicyclo[3.2.1]octane (D27) as a mixture of the axial (D26) and equatorial (β) (D28) isomers (ca. 60:40) as shown by proton magnetic resonance spectrum.

DESCRIPTION 4C

3α-amino-8-butyl-8-azabicyclo[3.2.1]octane (D29); intermediate for Compound 27

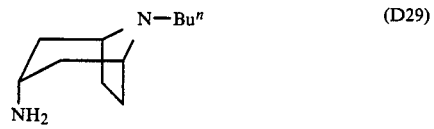

N-n-butylnortropinone (5.0 g, 0.028 mole) in ethanol (50 ml) was treated with ethanolic ammonia and left to stand for 24 hours. The mixture was hydrogenated over Raney nickel for 24 hours at 300 p.s.i. in the presence of ammonium acetate (2.5 g.). The mixture was filtered, evaporated in vacuo, treated with H₂O, and extracted with ethyl acetate. The combined organic extracts were acidified and separated. Basification of the aqueous layer and further extraction with ethyl acetate yielded (D29) (2.55 g., 50%), after drying (K₂CO₃) and evaporated in vacuo which was used without further purification.

DESCRIPTION 5

2-aminomethyl-8-methyl-8-azabicyclo[3.2.1]octane (D31); intermediate for Compound 37

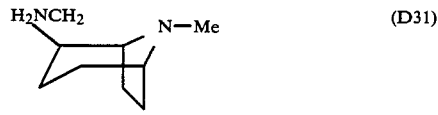

including all isomeric forms.

Methyl isocyanide (5.04 g., 0.026 mol) was added to (±)-tropan-2-one (2 g., 0.0143 mol) in dimethoxyethane (80 ml) and the solution cooled to 0° C. Ethanol (2 ml) was added followed by addition of potassium tert-butoxide (5.64 g, 6.05 mol). The mixture was then heated at 50° C. for three hours, cooled and poured into a saturated potassium carbonate solution (300 ml). This was extracted with ethyl acetate (3×100 ml) and the combined extracts dried (K₂CO₃), filtered and evaporated to give a crude oil which was abosorbed on alumina (40 g, grade 1 neutralised by addition of 10% water) from ethereal solution. The solution was eluted with a progressively graded mixture of ether, ethyl acetate and methanol to give 8-methyl-8-azabicyclo[3.2]octane-2 nitrile (1.1 g-46%) as an oil.

The nitrile (1.1 g) in tetrahydrofuran (20 ml) was added to lithium aluminium hydride (0.5 g) in tetrahydrofuran (30 ml) and the mixture stirred for three hours. Water (0.5 ml), sodium hydroxide solution (10%) (0.75 ml) and water (1.25 ml) were added successively and the mixture filtered. The filtrate was dried (K₂CO₃) and evaporated to give crude (D31) (1 g) as an oil.

The product is a racemate of a single diastereomer, believed to be the (±)-α-isomer.

DESCRIPTION 6

Pentachlorophenyl 5-chloro-2-methoxy-4-methylaminobenzoate (D32)

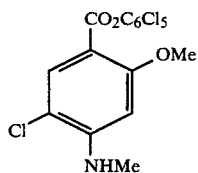

5-chloro-2-methoxy-4-methyl benzoic acid (2 g., 0.0093 mol) in dimethylformamide (50 ml) was treated with pentachlorophenyl trichloroacetate (4.5 g., 0.11 mol) and triethylamine (1.5 ml). The mixture was stirred at room temperature for one hour. The dimethylformamide was stripped off in vacuo, and the residue recrystallised from acetone/petroleum to give pentachlorophenyl 5-chloro-2-methoxy-4-methylaminobenzoate, m.pt 217°–219° C.

EXAMPLE 1

4-acetamido-5-chloro-2-methoxy-N-(3α,β-[4'-benzyl]-8-azabicyclo[3.2.1]octyl)-benzamide (1)

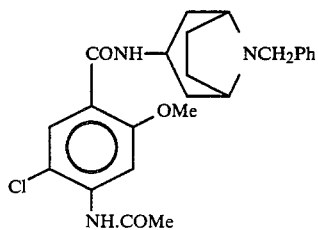

To 4-acetamido-5-chloro-2-methoxybenzoyl chloride (6 g) in toluene (200 ml) and triethylamine (5 ml) was added 3αβ-amino-8-benzylnortropane (D1) (4.2 g) (prepared as in Description 1) in toluene (20 ml). The reaction mixture was stirred at room temperature for 2 hours. The mixture was treated with 2.5N aqueous sodium hydroxide (20 ml), the toluene layer was separated and the aqueous layer was extracted with chloroform (3×150 ml) and the combined organic extracts were dried (K$_2$CO$_3$). The solvent was removed therefrom and chromatography of the product (neutral alumina, Brockman II, ethyl acetate eluant) gave a mixture of 3'α and 3'β isomers of (1) as an oil (7.2 g, 84%).

EXAMPLE 2

4-amino-5-chloro-2-methoxy-N-(3'α,8-[8'-benzyl]8-azabicyclo[3,2,1]octyl)benzamide (2) and 4-amino-5-chloro-2-methoxy-N-(3',α-8'-benzyl]nortropyl)benzamide (3)

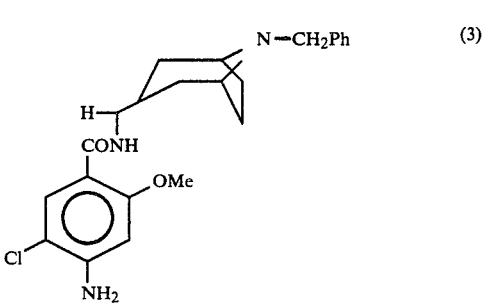

(1) (7.2 g) (prepared as in Example 1) was refluxed with an aqueous ethanol (water 10 ml ethanol (100 ml)) solution of potassium hydroxide (2 g) for 3 hours. The mixture was then cooled to room temperature. The ethanol was removed by rotary evaporation. The residue was extracted with chloroform. The organic extracts were chromatographed (neutral alumina, Brockman II, ethyl acetate eluant) Bands containing (2) and (3) respectively were obtained, yielding (2) (3.3 g, 50%) and (3) (2.0 g, 30%).

(2) was shown by n.m.r. to be a 2:3 weight ratio mixture of the 3'α and 3'β isomers, and had a m.pt 159°–70° C.

Compound (3):

m.p.t. 221°–3° C. n.m.r. (δ, CDCl$_3$): 8.10(s, 1H, aryl 6—H) 7.6–7.1 (m, 6H, Ph—H and CONH), 6.30 (s, 1H, aryl 3—H), 4.6–4.2 (m, 3H, —NH$_2$, CONH.CH=), 3.93 (s, 3H, OCHH$_3$), 3$\frac{1}{2}$56 (s, 2H, PhCH$_2$.N=), 3.4–3.1 (m, 2H, =CH—N(CH$_2$Ph)—CH=), 2.3–1.5 (m, 8H, =CH$_2$).

EXAMPLE 3

4-acetamido-5-chloro-2-methoxy-N-(3'β-[8'-benzyl]8-azabicyclo[3.2.1]octyl)benzamide (4)

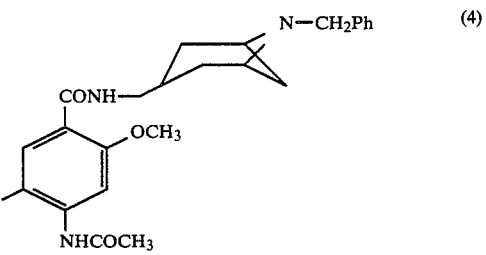

A solution of 4-acetamido-5-chloro-2-methoxybenzyl chloride (1.6 g) in toluene (100 ml) and triethylamine (2 ml) was treated with a solution of crude 3β-amino-8-benzylnortropane (D4) (1.1 g) (prepared as in Description 2) in toluene (20 ml), and the reaction was stirred at room temperature for 2 hours. The mixture was treated with 2.5N aqueous sodium hydroxide solution (5 ml), the toluene layer was separated and the aqueous layer was extracted with ethyl acetate (3×50 ml). The solvent was removed from the combined, dried (K₂CO₃) organic extracts to give an oil which crystallised on trituration with diethyl ether, furnishing 4-acetamido-5-chloro-2-methoxy-N-(3'β-[8'-benzyl]nortropy)benzamide (4) (1.5 g, 70%). m.p.t. 185° C.

EXAMPLE 4

4-amino-5-chloro-2-methoxy-N-(3'β-[8'-benzyl]8-azabicyclo[3.2.1]octyl)benzamide (5)

Compound (4) (prepared as in Example 3) (1.5 g) was hydrolysed in an aqueous ethanol (water 2 ml, ethanol 20 ml) solution of potassium hydroxide (0.5 g) under reflux for 2 hours, and the mixture was then diluted with water (50 ml), and then cooled to ambient temperature. The resulting precipitate was collected, dried and recrystallised (ethyl acetate/petrol) to give pure 4-amino-5-chloro-2-methoxy-N-(3'β-[8'-benzyl]8-azabicyclo[3.2.1]octyl)benzamide (5) (1.1 g, 80%) m.p.t. 188° C.

n.m.r. (δ CDCl₃): 8.08 (s, 1H, aromatic 6—$\underline{H}$), 7.60–7.10 (m, 6H, C₆$\underline{H}_5$ and CON$\underline{H}$), 6.28(s, 1H, aromatic 3—$\underline{H}$), 4.6–4.2 (m, 3H, —N$\underline{H}_2$ and CONH.C$\underline{H}$=), 3.87 (s, 3$\underline{H}$, OC$\underline{H}_3$), 3.56 (S, 2H, PhC$\underline{H}_2$), 3.4–3.1 (m, 2$\underline{H}$=C$\underline{H}$—N(CH₂Ph)—C$\underline{H}_2$), 2.3–1.5(m, 8H—C$\underline{H}_2$).

EXAMPLE 5

4-Amino-5-chloro-2-methoxy-N-(3'β-[8'-benzyl]-8-azabicyclo[3.2.1]octyl)benzamide (5)

Following the procedures outlined in Example 4 above, the crude 3β-amino-8-benzyl-nortropane (D5) was converted to pure 4-amino-5-chloro-2-methoxy-N-(3'β-[8'-benzyl]-nortropyl)-benzamide (5)(64%), m.p. 188°–9° C. This was identical to that obtained (n.m.r. and mixed mp.) in Example 4 above.

Nomenclature note: Nortropyl≡(8-azabicyclo-[3,2,1]-octyl).

EXAMPLE 6

4-Amino-5-chloro-2-methoxy-N-(3'β-[8'-methyl-8'-azabicyclo[3.2.1]-octyl])-benzamide (19)

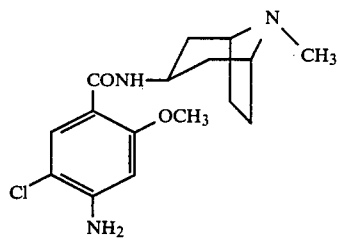

4-Acetylamino-5-chloro-2-methoxy benzoic acid (4.0 g; 0.016 mole) was dissolved in thionyl chloride (40 ml) at 30°, evaporated in vacuo and azeotroped twice with anhydrous toluene (ca. 100 ml). The resulting 4-acetylamino-5-chloro-2-methoxy benzoyl chloride was redissolved in warm anhydrous toluene (ca. 100 ml) treated with triethylamine (5 ml) and 3β-aminotropane (prepared above). The reaction mixture was stirred at room temperature for 2 hours. The mixture was treated with 2.5N sodium hydroxide (20 ml), the toluene layer was separated and the aqueous layer extracted with chloroform. The combined extracts were evaporated in vacuo and the resulting solid refluxed with an aqueous ethanol (water 5 ml; ethanol 50 ml) solution of potassium hydroxide (2.5 g) for 1½ hours. The mixture was cooled, ethanol removed in vacuo and the mixture extracted with warm chloroform (5×100 ml). The combined organic extracts were dried (K₂CO₃) filtered and evaporated in vacuo. Recrystallisation of the resulting solid gave 4-amino-5-chloro-2-methoxy-N-(3'β-[8-methyl-8-azabicyclo[3.2.1]-octyl])-benzamide (1.3 g; 30%) as colourless microcrystals, m.p. 249°–250°.

The following compounds were prepared in an analogous manner:

Compounds in Table B with A suffixed are the 4-acetylamino condensation products, prior to base hydrolysis to give the corresponding compound of the unsuffixed number.

TABLE B

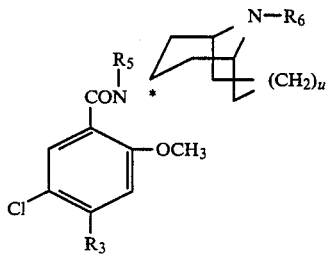

| Compound No. | From Intermediate | R₆ | isomer u | * | R₅ | R₃ | m. pt °C. |
|---|---|---|---|---|---|---|---|
| 6 | + D26 | 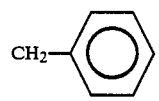 | 0 | α | Me | NH₂ | 172.5 |

TABLE B-continued

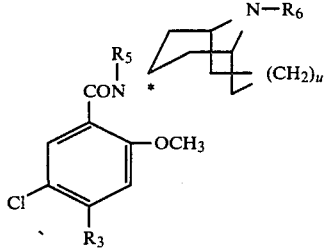

| Compound No. | From Intermediate | $R_6$ | u | isomer * | $R_5$ | $R_3$ | m. pt °C. |
|---|---|---|---|---|---|---|---|
| 11 | D10 § | $CH_2$-phenyl | 1 | α | H | $NH_2$ | 199 |
| 13 | D12 | $CH_2$-(4-Me-phenyl) | 0 | β | H | $NH_2$ | 213–5 |
| 14 | D13 | $CH_2$-(4-OMe-phenyl) | 0 | β | H | $NH_2$ | 175–8 |
| 15 | D14 | $CH_2$-(4-OEt-phenyl) | 0 | β | H | $NH_2$ | 164–6 |
| 16 | D5 | $CH_2$-(4-Cl-phenyl) | 0 | β | H | $NH_2$ | 212–3 |
| 17 | D6 | $CH_2$-(3,4-diCl-phenyl) | 0 | β | H | $NH_2$ | 191–5 |
| 18 | D15 | $CH_2CH_2Ph$ | 0 | β | H | $NH_2$ | 222 |
| 18A | D15 | $CH_2CH_2Ph$ | 0 | β | H | NHAc | 224 |
| 20 | D26 | Me | 0 | α | H | $NH_2$ | 219–220 |
| 20A | D26 | Me | 0 | α | H | NHAc | 178–9 |
| 21 | D25 | Me | 1 | α* | H | $NH_2$ | 218–220 |
| 22 | D16 | Me | 1 | β* | H | $NH_2$ | 208–9 |
| 23+ | D17 | Et | 0 | β | H | $NH_2$ | 187 |
| 23A | D17 | Et | 0 | β | H | NHAc | 157 |
| 24 | D18 | $Pr^n$ | 0 | β | H | $NH_2$ | 205 |
| 24A | D18 | $Pr^n$ | 0 | β | H | NHAc | 140 |
| 25 | D19 | $Pr^i$ | 0 | β | H | $NH_2$ | 183 |
| 26 | D20 | $Bu^n$ | 0 | β | H | $NH_2$ | 224–6 |
| 27 | D29 | $Bu^n$ | 0 | α | H | $NH_2$ | 205–6 |
| 28 | D21 | $CH_2Pr^i$ | 0 | β | H | $NH_2$ | 206–7 |
| 29 | D22 | CH(Me)Et | 0 | β | H | $NH_2$ | 195–7 |
| 30 | D23 | $CH_2$-cyclohexyl | 0 | β | H | $NH_2$ | 253–4 |
| 31 | D24 | cyclohexyl | 0 | β | H | $NH_2$ | 278 |

TABLE B-continued

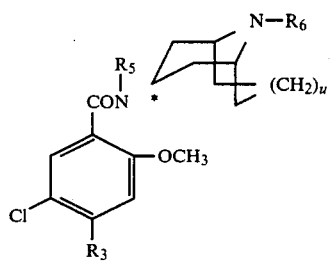

| Compound No. | From Intermediate | R₆ | u | isomer * | R₅ | R₃ | m. pt °C. |
|---|---|---|---|---|---|---|---|
| 31A | D24 |  | 0 | β | H | NHAc | 207 |
| 32 | D30 | CH₂CH=CH₂ | 0 | β | H | NH₂ | 173–5 |

+ Prepared as described in Description 4A
§ Prepared as described in Description 3D
⁺ as the crystalline hemi-hydrate
*provisional assignment The following Compounds may be prepared analogously:

5-chloro-2-methoxy-4-methylamino-N-(3'-[8'-benzyl-8'-azabicyclo[3.2.1]octyl])benzamide (33)

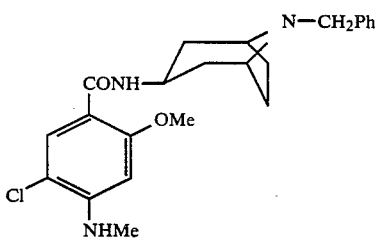 (33)

4-amino-5-chloro-2-methoxy-N-([2'-(±)-[8'-benzyl-8'-azabicyclo[3.2.1]octyl]methyl)benzamide (34)

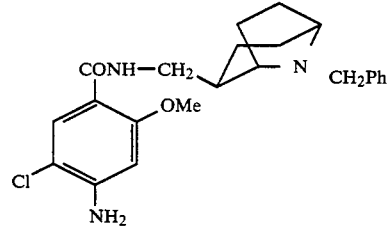 (34)

including all isomeric forms 4-amino-5-chloro-2-methoxy-N-(2'-(±)-[7'-benzyl]-7'-azabicyclo[2.2.1]heptyl)benzamide (35)

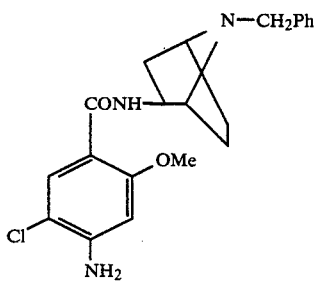 (35)

including all isomeric forms 4-amino-5-chloro-2-methoxy-N-(3'β-(±)-9'-benzyl-9'-azabicyclo[4.2.1]nonylbenzamide (36)

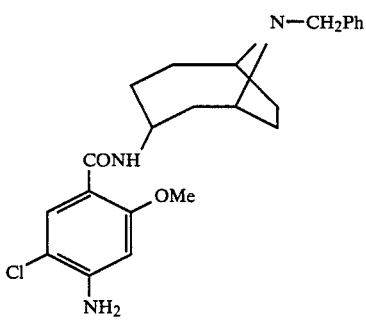 (36)

including all isomeric forms

EXAMPLE 7

4-Amino-5-chloro-2-methoxy-N-methyl-N-(3'α-[8'-benzyl-8'-azabicyclo[3.2.1]octyl)benzamide, (6), and 4-amino-5-chloro-2-methoxy-N-methyl-N-(3'β-[8'-benzyl-8'-azabicyclo[3.2.1]octyl)benzamide, (7)

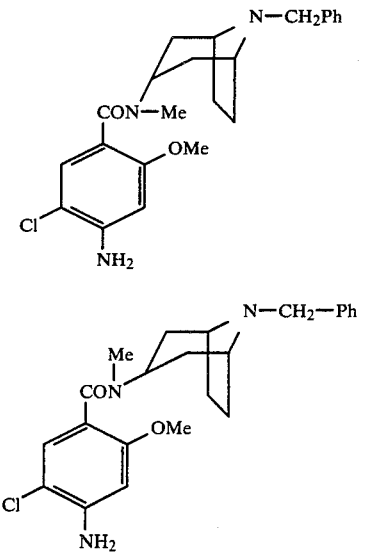

Treatment of (D 27) prepared as in Description 4B with 4-acetylamino-5-chloro-2-methoxy-benzoyl chloride and hydrolysis as outlined in Example 6 gave 4-amino-5-chloro-2-methoxy-N-methyl-N-(3β-[8-benzyl-8-azabicyclo-[3.2.1])benzamide (7), m.p. 180° and 4-amino-5-chloro-2-methoxy-N-methyl-N-(3α-[8-benzyl-8-azabicyclo-[3,2,1]-octyl])-benzamide (6), m.p. 173° separated by chromatographic elution with ether/ethyl acetate from silica.

The latter compound was identical with Compound 6 prepared in Example 6 from the α-amino intermediate (D 26), in turn prepared as in Description 4A.

EXAMPLE 8

5-Sulphamoyl-2-methoxy-N-(3'β-[8'-benzyl]-8'-azabicyclo-[3.2.1]octyl)-benzamide (8)

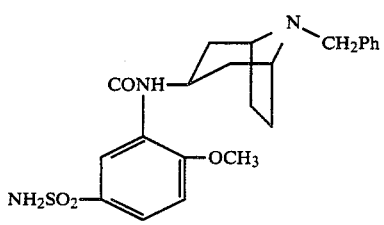

5-sulphamoyl-2-methoxybenzoic acid (2.0 g., 0.009 mole) was dissolved in anhydrous dimethylformamide (20 ml), treated with triethylamine (0.83 g, 0.009 mole) and cooled to 0°. Ethylchloroformate (0.95 g., 0.009 mole) was added dropwise and the solution left to stir for 15 minutes. 3β-Amino-8-benzyl-8-azabicyclo-[3.2.1]-octane (D4) (1.9 g., 0.09 mole) [prepared as outlined in Description 3B] was added in one portion at 0°. The mixture was left to stand overnight, evaporated to dryness, treated with water (5 ml) and dilute ammonia (10 ml) to give 5-sulphamoyl-2-methoxy-N-(3'β-[8-benzyl-8-azabicyclo-[3,2,1]-octyl]-benzamide (38%), m.p. 213°–214°.

EXAMPLE 9

2-Methoxy-N-(3'β-[8'-benzyl-8'-azabicyclo-[3.2.1]-octyl])benzamide (9)

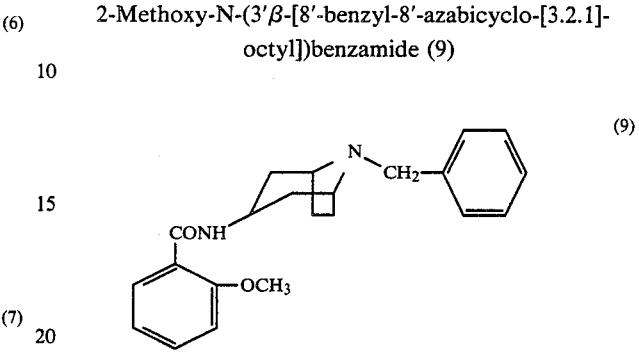

3β-Amino-8-benzylnortropane (D4) (1.01 g., 4.67 mmoles) in dry toluene (15 ml) was added to a solution of 2-methoxybenzoyl chloride (made by the reaction of thionyl chloride with 0.78 g. anisic acid) in dry toluene containing 2 ml of triethylamine. The mixture was stirred at ambient temperature for 12 hours then poured into water which was made alkaline by the addition of solid sodium carbonate. The mixture was extracted with ethyl acetate (3×200 ml). Subsequent drying (Na$_2$SO$_4$) and removal of solvent followed by chromatography on silica gel gave the pure 2-methoxy-N-(3'β-[8'-benzyl-8'-azabicyclo-[3.2.1]-octyl)benzamide (1.03 g., 63%) as an oil, m.pt. (HCl salt) 269° C.

EXAMPLE 10

4-Amino-5-chloro-2-methoxy-N-(3'β-[8'-benzyl-8'-azabicyclo[3.2.1]octyl)-benzamide methobromide (10)

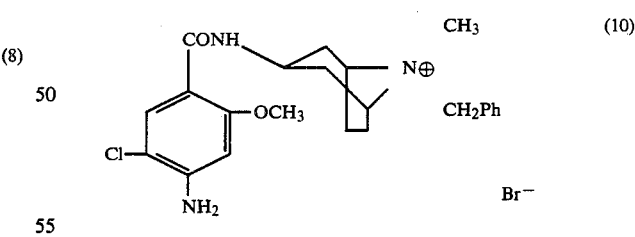

Bromomethane (5 ml) was added to 4-amino-5-chloro-2-methoxy-N-[3β'-(8'-benzyl-nortropyl)]-benzamide (6) (1.0 g) in anhydrous acetone (50 ml) and the solution allowed to stand at ambient temperature for 3 days. The solid produced was filtered off and recrystallized from methanol/ethyl acetate to give 4-amino-5-chloro-2-methoxy-N-[3β-(8-benzyl-8-azabicyclo[3.2.1]octyl)-benzamide methobromide (0.63 g; 53% m.p. 222°–5°.

EXAMPLE 11

4-Amino-5-chloro-2-methoxy-N-(3'α-[9'-azabicyclo[3.3.1]nonyl)benzamide (11) and 4-amino-5-chloro-2-methoxy-N-(3'β-[9'-benzyl-9'-azabicyclo-[3.3.1]nonyl])-benzamide (12)

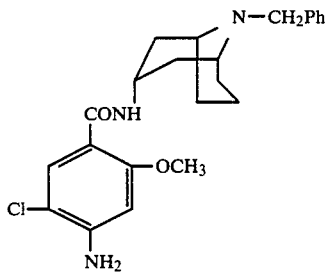

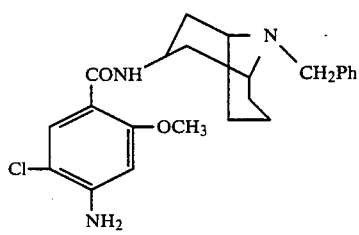

Reaction of 3αβ-amino-9-benzyl-9-azabicyclo[3.3.1]nonane (D9) prepared as in Description 3B with 4-acetylamino-5-chloro-2-methoxy-benzoyl chloride and hydrolysis as outlined in Example 6 gave 80-90% 4-amino-5-chloro-2-methoxy-N-(3'β-[9'-benzyl-9'-azabicyclo-[3.3.1]-nonyl]-benzamide (12) m.p. 224°-225° and 10-20% 4-amino-5-chloro-2-methoxy-N-(3'α-[9'-benzyl-9'-azabicyclo-[3.3.1]-nonyl]-benzamide (11) m.p. 199°, separated by chromatographic elution from silica with ethyl acetate/petrol-ether 60°-80°.

The latter compound, m.p. 199°, is indentical to Compound 11 prepared in Example 6 from the α-amine (D10), in turn prepared as in Description 3D.

EXAMPLE 12

4-Amino-5-chloro-2-methoxy-N(2'-(±)-[8'-methyl-8'-azabicyclo[3.2.1]octyl]methyl)benzamide (37)

This compound was prepared analogously to Example 6 from (D 31).

M.pt. 218°-9° C.

The product is a racemate of a single diastereomer, believed to be the (±)-α-isomer.

EXAMPLE 13

5-chloro-2-methoxy-4-methylamino-N-[3β-(8'-benzyl-9'-azabicyclo-(3.2.1)octyl)]benzamide (33)

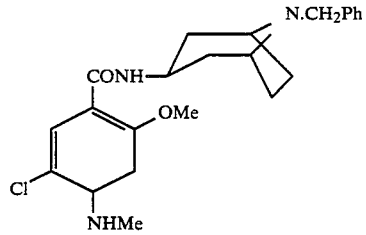

Pentachlorophenyl 5-chloro-2-methyoxy-4-methylamino)benzamide (D32) (1 g.) was treated with 3β-amino-8-benzyl-8-azabicyclo(3.2.1)octane (0.47 g) in dimethyl formamide (15 ml) at 80° for 24 hours. The mixture was evaporated to a thin film, then poured into stirred water. The white crystals were filtered, dried in vacuo and chromatographed on 5% deactivated alumina (Brockman 1) using ethyl acetate as eluant. The recovered material was recrystallized from ethyl acetate and light petroleum 60/80 to give 5-chloro-2-methoxy-4-methylamino-N[3β-(8'-benzyl-8'-azabicyclo(3.2.1)octyl)]benzamide, m.pt 156°-157° C.

PHARMACOLOGICAL DATA

The following Section illustrates the pharmacological activity of compounds of the formula (I).

I. Dopamine Receptor Blocking Activity in the Central Nervous System (a) Inhibition of apomorphine induced stereotype behaviour in the rat (method of Ernst (1967), Psychopharmacologia (Berl.) 10 316-323). Table I shows the dose for complete inhibition.

Compounds marked IA ( ) are inactive at the dose in the brackets, mg/Kg s.c.

(b) Inhibition of apomorphine induced climbing in the mouse The test is based on that described by Protais, P., Constantin, J. and Schwartz J. C. (1976), Psychopharmacology, 50, 1-6.

Apomorphine 1 mg/kg s.c. induces mice to climb the wall of a wire cage (inverted food hopper—11×7.5×18 cm high). Mice acclimatised in their home cages in groups of 5 are placed under the hoppers immediately after the injection of apomorphine 1 mg/kg s.c. At 10, 20 and 30 minutes after injection climbing behaviour is scored. The mice are observed for 30 seconds and scored according to the position they spend the majority of time in, score 0—four paws on floor of cage; score 1—fore paws only on walls; score 2—all paws on wall of cage. The scores at all 3 times and for each mouse are summed and mice drug treated orally compared to mice receiving apomorphine only. A saline only treated group is also included and any score, generally <5% of maximum taken into account.

Table I shows the dose for complete inhibition, or the $ED_{50}$. Compounds marked IA were inactive at 10 mg/Kg p.o.

(c) In vitro displacement of radiolabelled spiroperidol from dopamine receptor membranes

[$^3$H]-spiroperidol has been shown to bind with high affinity to dopamine receptors in the brain (Greese, I., Schneider, R. and Snyder, S. H., European J. Pharmac., 46 [1977], 377-381; Leysen, J. E., Gommeren, W. and Laduron, P. H. Biochem. Pharmac., 27, [1978]. 307-316). Therefore a compound which displaces this ligand from dopamine receptor membranes may have neuroleptic properties.

Male Hooded Lister rats (200-300 g) are decapitated and the caudate nucleus is quickly dissected out. This is homogenised in ice cold Tris buffer (pH 7.7 at 25° C.) at a concentration of 10 mg/ml wet weight of tissue. The test compound (at $10^{-5}$M) or spiroperidol (standard curve from $10^{-5}$ to $10^{-9}$M) is added to the assay tubes followed by 0.5 nM [$^3$H]-spiroperidol. This is mixed with 500 μl of the membrane preparation and the assay tubes are incubated for 15 minutes at 37° C. After this period 4 ml ice cold Tris buffer is added to each tube and the solutions are filtered through pre-soaked glass fibre filters. The filter is washed twice with 4 ml of the buffer and then transferred to a scintillation vial for counting. Single concentration results are given as a percentage of [$^3$H]-spiroperidol displaced. Table I shows the percentage displacement at $10^{-5}$M concentration of the compound, or the concentration for 50% displacement (ED$_{50}$). Compounds displacing less than 50% at $10^{-5}$M are not shown in Table I.

II. Anti-emetic activity in the dog

Compounds were administered subcutaneously 30 minutes prior to administration of a standard dose of apomorphine HCl (0.1 mg/kg subcutaneously) and the vomiting response compared to that obtained when the same animals were dosed with apomorphine HCl and vehicle only. The dose that totally inhibited the vomiting response was determined in the same instances, the ED$_{50}$ in others.

III. Gastric Activity (a) Increase in intragastric pressure in the rat

Intragastric pressure changes were recorded from previously starved conscious but restrained rats using a saline filled catheter inserted into the lumen of the stomach via a permanent gastric fistula. The catheter was connected to a physiological pressure transducer and pressure changes recorded on a hot wire pen recorder. In each animal a pre-dose period of 40 minutes was allowed to obtain a measure of spontaneous activity. An index of activity was obtained by measuring the average height of pressure waves during 10 minute periods. Values for 4 such periods were obtained during assessment of spontaneous activity and for the 40 minute period after the subcutaneous administration of the compounds. Students 't' test was applied to the difference in average values obtained for spontaneous and post-compound activity.

Table II shows the minimum dose for activity. Compounds marked IA ( ) are inactive at the dose in the brackets, mg/Kg s.c.

(b) Increase in gastric emptying: reversal of apomorphine induced delay in gastric emptying in the rat Rats equipped with chromic gastric fistulae were used and it was through this that 5 ml of a test meal (5 ml phosphate buffer at pH 9) was administered and recovered. The % recovery of the standard meal after remaining in the stomach for 10 minutes was taken as an index of gastric emptying. Delay in gastric emptying was induced by the administration of apomorphine HCl (5 mg/kg subcutaneously) which was given 15 minutes prior to the subcutaneous administration of the compound. The % recoveries of the test meal were determined at 15-25 and 45-55 minutes post-dosing with the compound and compared with vehicle only dosed animals set up simultaneously. Six animals were used for each group.

Table II shows the % increase in gastric emptying for 10 mg/kg s.c. of the compound.

In addition the % recoveries for compound 2 are shown in the Table immediately below.

TABLE

| Treatment | % Recovery of test meal. Mean values ± S.E. of mean Time interval post dosing with vehicle or compounds | |
|---|---|---|
| | 15-25 mins. | 45-55 mins. |
| (1) Apomorphine + vehicle | 72.4 ± 5.1 | 60.7 ± 7.3 |
| (2) Apomorphine + vehicle (2) 10 mg/kg s.c. | 37.4 ± 6.7** | 18.3 ± 1.1*** |

Significantly different from apomorphine+vehicle group set up simultaneously  p<0.01 * p<0.001.

At 10 mg/kg subcut. the % recovery of test meal was significantly decreased at both the 15-25 and 45-55 minute time intervals and therefore gastric emptying was increased.

Compound 5 significantly increases gastric emptying at a dose of 0.05 mg/kg s.c.

TABLE I

| Compound | I(a) Dose Inhibiting Stereotype Behaviour mg/kg s.c. | I(b) Anti-Climbing Activity Dose mg/kg p.o. Complete Inhibition | ED$_{50}$ | I(c) Spiroperidol Displacement % at $10^{-5}$M | ED$_{50}$-7 M × 10 |
|---|---|---|---|---|---|
| 2 | 10 § | | | | |
| 3 | 50 § | | | | |
| 5 | 0.05 | | 0.03 | | |
| 6 | IA(50) | IA | | | |
| 8 | | IA | | | |
| 9 | | 10 | | | |
| 10 | | IA(2) | | | |
| 11 | IA(50) | IA | | | |
| 12 | 0.5 | 2 | | 53 | |
| 13 | | | 0.12 | 54 | |
| 14 | | 10 | | | |
| 15 | | 10 | | | |
| 16 | | 2 | | | |
| 18 | IA(50) | IA | | | 6 |
| 19 | IA(25) | IA | | 64 | |
| 21 | IA(50) | 10 | | | |
| 22 | IA(25) | IA | | | |
| 23 | IA(25) | IA | | | |
| 24 | IA(25) | IA | | | |
| 25 | IA(25) | IA | | | |
| 26 | + | | 2.9 | | 4 |
| 27 | IA(10) | IA | | 66 | |
| 28 | | | | | |
| 30 | * | 5 | | | 2 × $10^{-1}$ |
| 31 | | IA | | | |

§ lower levels not tested;
+ slight at 1;
* slight at 0.05

TABLE II

| Compound | II Anti-Emetic Activity Dose, mg/kg s.c. | | III(a) Increase in Intragastric Pressure | III(b) Increase in Gastric Emptying |
|---|---|---|---|---|
| | Complete Inhibition | ED$_{50}$ | Dose, mg/kg s.c. | % |
| 2 | 0.0025 | | | |
| 3 | 0.05 | | | + |
| 5 | 0.001 | | | |
| 6 | | | 10 | IA(50) |

TABLE II-continued

| Compound | II Anti-Emetic Activity Dose, mg/kg s.c. Complete Inhibition | $ED_{50}$ | III(a) Increase in Intragastric Pressure Dose, mg/kg s.c. | III(b) Increase in Gastric Emptying % |
|---|---|---|---|---|
| 8 | 0.1 | | IA(5) | |
| 9 | 0.1 | | | |
| 10 | IA | | 0.25 | |
| 11 | IA | | 1 | |
| 12 | 0.1 | | IA(1) | |
| 13 | 0.1 | | | |
| 14 | 0.1 | | | |
| 15 | 0.1 | | | |
| 16 | | | | |
| 18 | 0.25 | | IA(5) | |
| 19 | 1.6 | | 1–10 | 25 |
| 21 | | | 5 | |
| 22 | | | 1 | IA(25) |
| 23 | 1.6 | | 1–10 | 25 |
| 24 | 0.4 | | 5–10 | IA(25) |
| 25 | | 0.8 | 5 | IA |
| 26 | 0.4 | | | 1 |
| 27 | 1 | | IA(10) | IA(10) |
| 28 | 0.2 | | 5 | |
| 30 | * | | IA(1) | 0.05 |
| 31 | 0.25 | | | |
| 32 | 0.2 | | | |

* slight at $5 \times 10^{-4}$;
+ see Pharmacolgical Data, III(b)

For the sake of completeness it should be mentioned that single compound tests have shown Compound 5 to have anti-obesity activity and Compound 20 to have antiarrhythmic activity.

Toxicity

In the tests reported above no toxic effects were observed.

What we claim is:

1. An azabicyclo (3.2.1) octane having the formula (XIII):

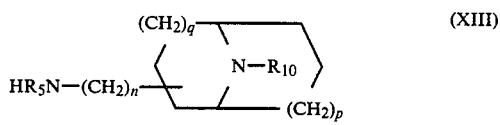

wherein n is 0, p is 0 and q is 1, $R_5$ is hydrogen, and $R_{10}$ is a group —$(CH_2)_t R_8$ wherein t is 1 or 2 and $R_8$ is a phenyl group optionally substituted by one or two substituents selected from $C_{1-6}$ alkyl, $C_{1-4}$ alkoxy, trifluoromethyl and halogen.

2. A compound according to claim 1 wherein the compound is the β-isomer.

3. 3-Amino-8-benzylnortropane.

4. 3β-amino-8-benzylnortropane.

5. 3-Amino-8-benzylnortropane in the form of a mixture of its α and β isomers.

* * * * *